United States Patent
Wehrman et al.

(10) Patent No.: US 8,865,421 B2
(45) Date of Patent: Oct. 21, 2014

(54) ASSAYS FOR NUCLEAR HORMONE RECEPTOR BINDING

(75) Inventors: Thomas S. Wehrman, Mountain View, CA (US); Chin Yee Loh, Kensington, CA (US); Mahesh Mathrubutham, Cupertino, CA (US); Keith R. Olson, Pleasanton, CA (US)

(73) Assignee: DiscoveRx Corporation, Fremont, CA (US)

( * ) Notice: Subject to any disclaimer, the term of this patent is extended or adjusted under 35 U.S.C. 154(b) by 805 days.

(21) Appl. No.: 12/489,642

(22) Filed: Jun. 23, 2009

(65) Prior Publication Data

US 2010/0151496 A1 Jun. 17, 2010

Related U.S. Application Data

(60) Provisional application No. 61/077,686, filed on Jul. 2, 2008.

(51) Int. Cl.
| | | |
|---|---|---|
| G01N 33/53 | (2006.01) | |
| C12N 5/00 | (2006.01) | |
| C12N 5/07 | (2010.01) | |
| G01N 33/78 | (2006.01) | |
| G01N 33/74 | (2006.01) | |

(52) U.S. Cl.
CPC .............. *G01N 33/743* (2013.01); *G01N 33/78* (2013.01); *G01N 2500/10* (2013.01)
USPC .............. 435/7.6; 435/7.8; 435/7.9; 435/325; 435/358

(58) Field of Classification Search
None
See application file for complete search history.

(56) References Cited

U.S. PATENT DOCUMENTS

| | | |
|---|---|---|
| 5,846,711 A | 12/1998 | Moore et al. |
| 5,846,722 A | 12/1998 | Kauvar et al. |
| 6,342,345 B1 * | 1/2002 | Blau et al. .................. 435/4 |
| 7,135,325 B2 | 11/2006 | Naqvi et al. |
| 7,479,377 B2 * | 1/2009 | Zhao et al. ................. 435/7.6 |
| 2003/0039980 A1 | 2/2003 | Thompson |
| 2003/0077664 A1 | 4/2003 | Zhao et al. |
| 2003/0092070 A1 | 5/2003 | Zhao et al. |
| 2003/0170765 A1 | 9/2003 | Rouhani et al. |
| 2004/0132038 A1 | 7/2004 | Fagan et al. |
| 2005/0130232 A1 | 6/2005 | Zhao et al. |
| 2006/0035813 A1 | 2/2006 | Sternberg et al. |
| 2006/0134670 A1 | 6/2006 | Piu |
| 2007/0218456 A1 | 9/2007 | Hanson |

OTHER PUBLICATIONS

Molenda et al 2003. Biology of Reproduction. 69:1449-1457.*
Mahesh Mathrubutham, et al., "Assay Tools for Nuclear Hormone Receptor Studies," Genetic Engineering & Biotechnology News, Sep. 15, 2008, vol. 28, No. 16.
Search Report from PCT/US09/48300, Mailed Sep. 16, 2009.
Written Opinion from PCT/US09/48300, Mailed Sep. 16, 2009.

* cited by examiner

*Primary Examiner* — Shulamith H Shafer
(74) *Attorney, Agent, or Firm* — David J. Aston; Peters Verny, LLP

(57) ABSTRACT

Methods and genetic constructs are provided for detecting the binding of nuclear hormone receptors to a coactivator/corepressor. The methods employ enzyme fragment complementation using fragments of β-galactosidase as the detection system. Cells are transformed to express the large fragment of β-galactosidase fused to a member of the complex with NHR for initiation of transcription and have it localized in the nucleus and to express the small fragment of β-galactosidase fused to the nuclear hormone receptor for binding to the member upon stimulation with a ligand.

14 Claims, 5 Drawing Sheets

ASSAYS FOR NUCLEAR HORMONE RECEPTOR BINDING

CROSS-REFERENCE TO RELATED APPLICATIONS

This application claims priority from U.S. Provisional Patent Application No. 61/077,686, filed on Jul. 2, 2008, which is hereby incorporated by reference in its entirety.

STATEMENT OF GOVERNMENTAL SUPPORT

None.

REFERENCE TO SEQUENCE LISTING

Applicants assert that the paper copy of the Sequence Listing is identical to the Sequence Listing in computer readable form found on the accompanying computer file. Applicants hereby incorporate the contents of the sequence listing by reference in its entirety.

BACKGROUND OF THE INVENTION

1. Field of the Invention

The field of this invention is the determination of the effect of changes of the environment of a cell on the binding of nuclear hormone receptors to form transcriptional regulatory proteins.

2. Related Art

Nuclear hormone receptors ("NHRs") are a significant group of proteins that act as transcription factors when bound to an agonist. The natural agonists are lipophilic compounds such as steroids. Nuclear hormone receptors, more commonly referred to as nuclear receptors, define a family of ligand activated transcription factors (Tenbaum et al, Int J Biochem Cell Biol, 29:1325-41 (1997); Willson et al, Mol Endocrinol, 16:1135-44 (2002)). Structurally, they are characterized by the presence of modular domains: a zinc-finger DNA binding domain, a ligand binding domain and two transcriptional activation domains AF-1 and AF-2, ligand-independent and ligand-dependent, respectively. Depending upon the nuclear receptor, monomers or dimers (homodimers or heterodimers with other nuclear receptors) constitute the functional effectors. This gene family regulates a wide variety of physiological functions and has thus a broad therapeutic potential ranging from metabolic, endocrinological diseases to neurological disorders, to cancer.

Nuclear receptors operate by recruiting an array of auxiliary polypeptides, denoted corepressors and coactivators (further described in Mol. Endocrinol. 1996 October; 10(10): 1167-77, incorporated by reference to further define the properties of these putative coregulatory factors), and it is these auxiliary proteins that mediate the molecular events that result in transcriptional repression or activation. For most nuclear receptors, this recruitment event is initiated upon the binding of the nuclear receptor to a ligand. It can be envisioned that certain ligands can only trigger the recruitment of a particular set of coactivators or corepressors and thus promote very selective effects. Furthermore, phosphorylation/dephosphorylation events can also affect the activity of the nuclear receptor itself and/or the auxiliary proteins. Similarly, it is plausible to assume that certain ligands exclusively responsive to such modifications could be identified. Generally speaking, these selective modulators would be of tremendous interest from a therapeutic standpoint, exhibiting maximized therapeutic value and minimum adverse effects.

Nuclear hormone receptors have been divided into four types: (I) Exist in the cytosol and upon ligand binding dissociates from heat shock proteins, homodimerizes, translocates to the nucleus, and binds to hormone response elements ("HRE") of the chromosome; (II) Exist in the nucleus, binds to the HRE as heterodimers (usually with RXR), complexed with corepressors, upon binding with ligand dissociates from corepressors and recruits coactivators; (III) Similar to Type 1 binding to DNA as a homodimer; (IV) Exists as monomers or dimers and upon ligand binding recruits coactivators. The heat shock protein family is further defined in J Biosci Bioeng. 2008 October; 106(4):324-36, incorporated herein by reference to further describe the heat shock protein family.

The first step in the characterization of ligand interaction with a cloned receptor is to express the receptor in a ligand sensitive form. While a few receptors can be expressed in easily manipulated model systems such as yeast and E. coli, the interactions of ligands with most receptors are influenced by post-translational modifications that are only present in mammalian cells. Moreover, many of these receptors require mammalian proteins to accurately transduce their biological effects. Thus for wide applicability, an assay system is best when it is based on cloned receptors expressed in a mammalian system.

Historically, the ability of ligands to interact with nuclear receptors has been evaluated by competition with a radiolabeled ligand for a binding site on the receptor. Such assays are popular because they involve relatively few steps. However binding assays have many limitations: (i) for many technical reasons, binding assays are performed in non-physiological conditions which can influence receptor pharmacology; (ii) agonists and antagonists cannot be reliably discriminated; (iii) only binding sites for which radiolabeled ligands are available can be studied; (iv) binding assays are not easily applicable to orphan receptors for which ligands haven't yet been identified; (v) purchase, handling and disposal of radioisotopes are major expenses; (vi) local governments are concerned about contamination; and (vii) the industry has primarily looked to assays where the result can be detected optically for high throughput screening.

In order to develop such modulating ligands, it is essential to have an effective screening assay. Such assays act to winnow the large number of compounds that are tested to provide a small class that is then tested in slower, less economical, screens. The initial screening should lend itself to robotics, have few false positives, require a minimum of steps in its protocols, and allow for sensitive determination. Over the years, a large number of systems, methods and reagents, have been developed for screening compounds for their effect on cellular proteins. One group of systems involves employing fused proteins, fusing the protein of interest to a detectable polyamide label.

In developing these assays, one cannot predict the effect of the fusion to the label on the functioning of the target protein. There can be disruption as to folding, interactions between the label and the target protein, effects on translocation and binding to other intracellular proteins, interference with the detection of the label, and the like. There is also the problem of sensitivity in that one should be able to detect at the concentration of the $EC_{50}$, which is generally below about 1 μM. One of the attractive systems involves enzyme fragment complementation, generally employing fragments of β-galactosidase, where the fragments may complex independently to form an active enzyme or require being fused to auxiliary binding proteins which complex, bringing the fragments together to form an active enzyme. The degree to which the fragments independently complex without the presence of the auxiliary binding proteins can substantially affect the success of the assay. In the case of NHRs, how one organizes the interaction of the fusion protein, the complexing of the members of the NHR transcription factor, and the coactivator can be crucial in providing an effective assay.

There is a substantial need for the development of assays for screening ligands for nuclear hormone receptors that are accurate, utilize the full length protein, are applicable to orphan targets, are dependable, and for which the operators have familiarity and for which there is a substantial history of know-how and show-how for acceptance and adoption of the assays.

U.S. patent applications and patents of interest include 2007/0218456; 2006/0134670; 2006/0035813; 2005/0130232; 2003/0077664; and U.S. Pat. No. 5,846,711. Scientific articles of interest include: Beck, et al 2008 Anal Biochem 373, 263-71; and Le Guevel and Pakdel 2001 Biotechniques 30, 1000-4.

BRIEF SUMMARY OF THE INVENTION

Methods and reagents are capable of being used for high throughput screening employing enzyme fragment complementation with β-galactosidase as the enzyme. Genetic constructs are employed for a first fusion protein of the small β-galactosidase fragment with the nuclear hormone receptor ("NHR") and for a second fusion protein of the large β-galactosidase fragment and a second molecule that forms a complex with the NHR (usually a coactivator) to form a transcriptionally active complex. The second moiety may be a second NHR member, heat shock protein or the coactivator/corepressor sequence that becomes localized to the nucleus. Mammalian cells are transformed with the constructs and the resulting mutant cells used in the assay protocol in the presence of a candidate ligand. The assays are found to be highly sensitive and capable of distinguishing ligand binding to the NHR receptor member.

DESCRIPTION OF THE SPECIFIC EMBODIMENTS

Figure 1:
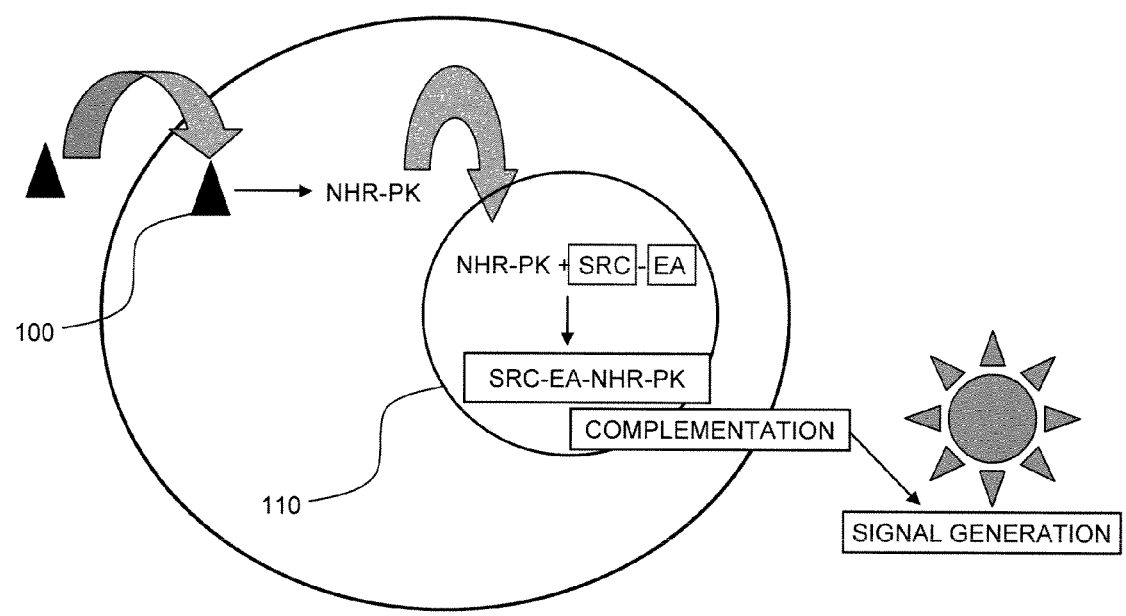
FIG. 1 is a cartoon of the assay mechanism; it shows the NHR PathHunter assays using protein-protein interaction strategy. SRC is the steroid receptor coactivator. The triangle represents the agonist. The activated NHR translocates to the nucleus, as shown in the figure at 100. The activated NHR-PK interacts with SCR 1EA in the nucleus of the cell at 110 to generate enzyme complementation by combining ED and EA.
Figure 2A:
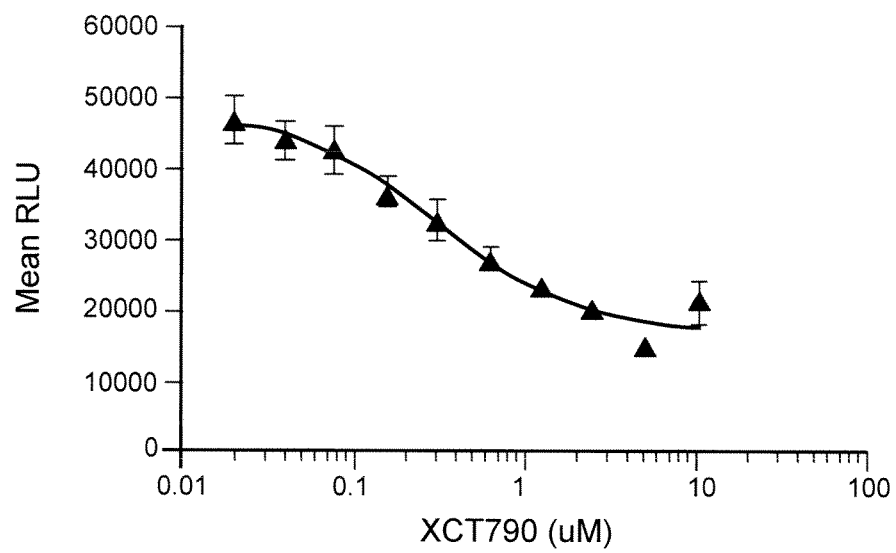
FIG. 2A is a graph of the results of the subject assay for ERRα (estrogen-related receptor α). It should be noted that ERRα is constitutively active and resides in the nucleus, so the assay is for an inverse agonist and is a loss of signal assay. It shows excellent performance for the CHO ERRα cell line. The data represents: stability to 20 passages; S/B=3 fold; EC50=300 nM; accurate pharmacology for inverse agonist. The ERRα is a constitutively active NHR and will reside in the nucleus under normal physiological conditions, making this a loss of signal assay.
Figure 2B:
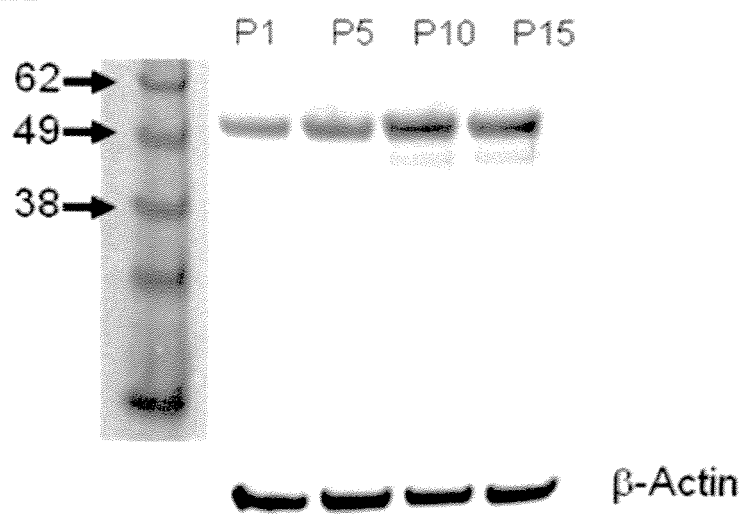
FIG. 2B is a photograph of a blot showing increased bands at the expected Mr of the expressed protein.
Figure 3A:
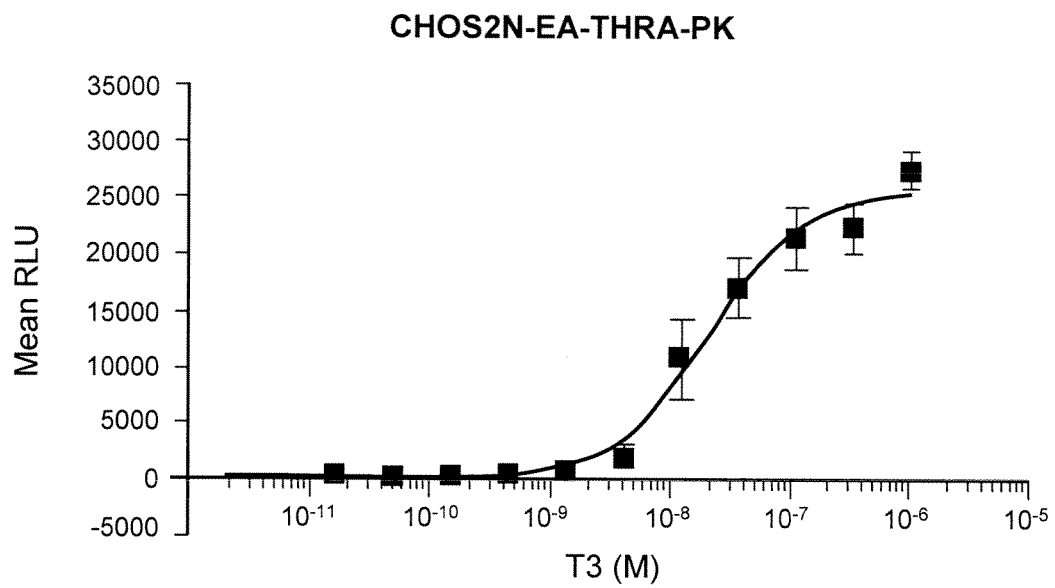
FIG. 3A is a graph of the results of the subject assay for THRα (thyroid hormone receptor α); it shows excellent performance for the THRα cell line. These data show: stability to passage 20; S/B=78 fold; EC50=15 nM and accurate pharmacology for the agonist. Shorter incubation times can be used. However, this results in higher EC50s and lower induction ratios. The cell conditioning involved first, the cells were grown in complete medium; second, they were washed in PBS twice; third, they were incubated in serum free medium overnight.
Figure 3B:
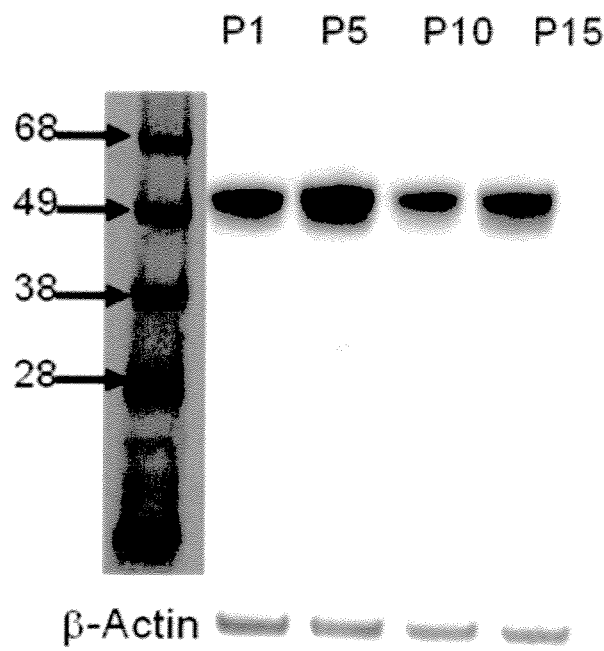
FIG. 3B is a blot as in FIG. 2B.
Figure 4A:
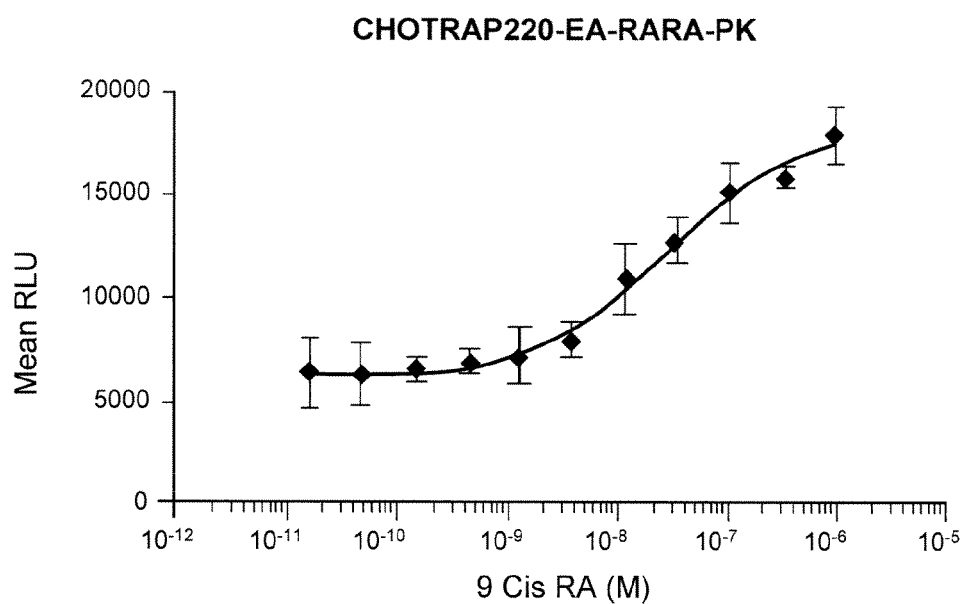
FIG. 4A is a graph of the results of the subject assay for RARα (retinoic acid receptor α); it shows excellent performance for the CHO RARα cell line. These data show: stability to passage 20; S/B=3 fold; EC50=29 nM and accurate pharmacology for the agonist. The cell conditioning involved first, the cells were grown in complete medium; second, they were washed in PBS twice; third, they were incubated in serum free medium overnight.
Figure 4B:
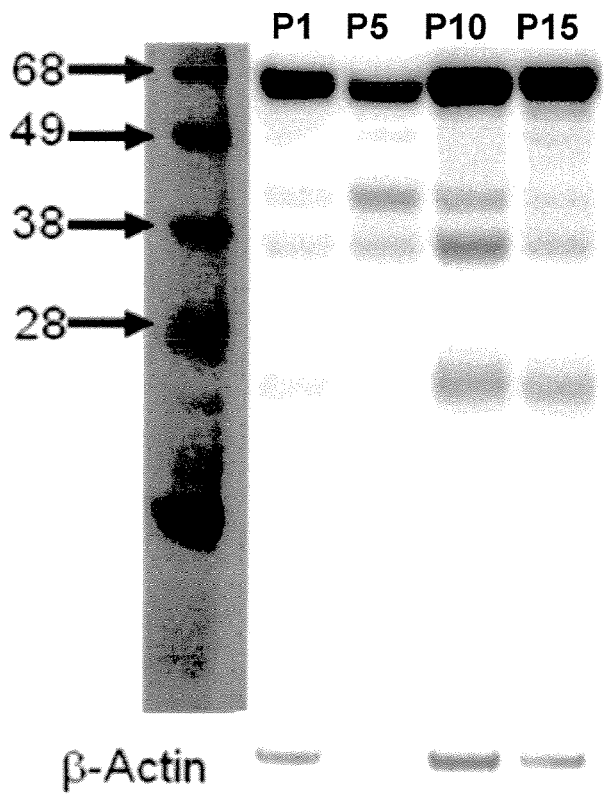
FIG. 4B is a blot as in FIG. 2B.
Figure 5A:
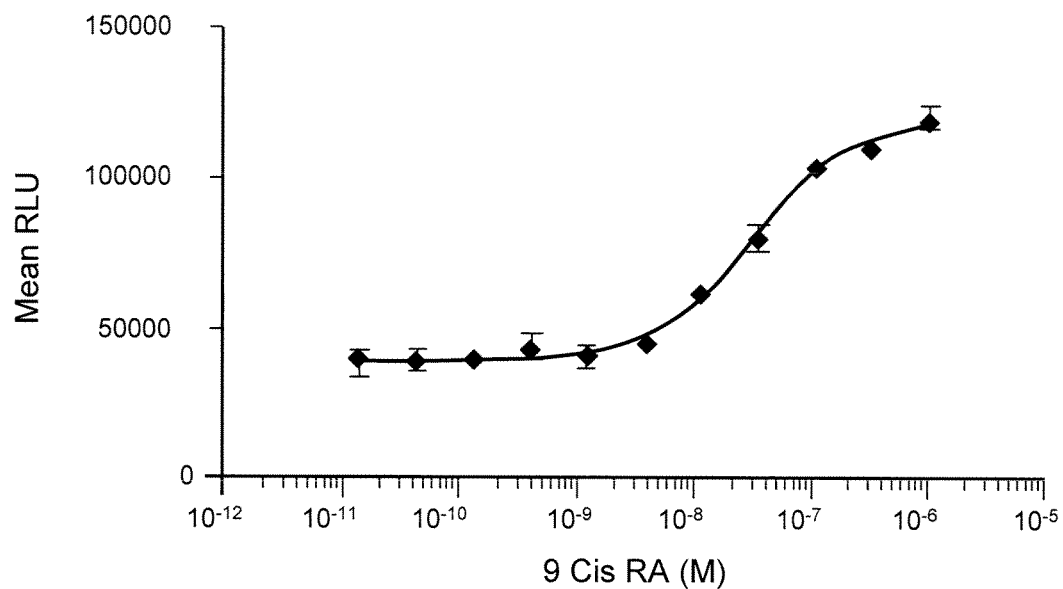
FIG. 5A is a graph of the results of the subject assay for RARβ (retinoic acid receptor β); it shows excellent performance for the CHO PGC1 RARβ cell line. These data show: stability to passage 20; S/B=3 fold; EC50=29 nM and accurate pharmacology for the agonist. The cell conditioning involved first, the cells were grown in complete medium; second, they were washed in PBS twice; third, they were incubated in serum free medium overnight.
Figure 5B:
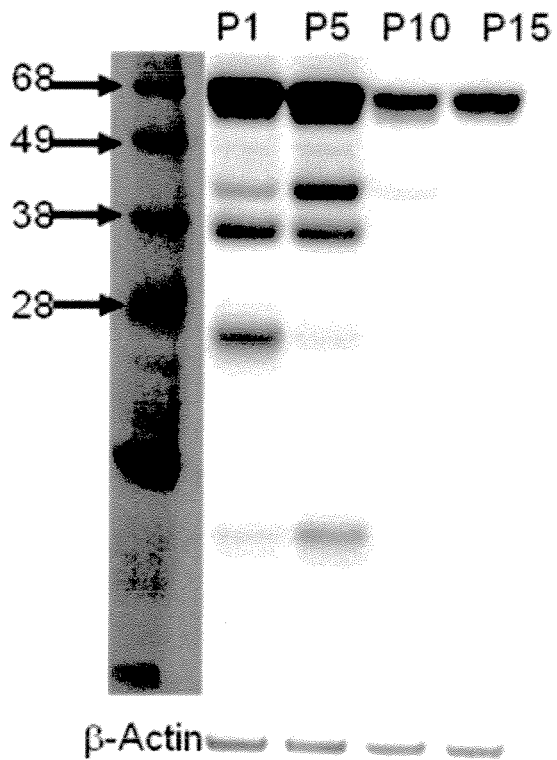
FIG. 5B is a blot as in FIG. 2B.

Ligands are capable of binding to NHRs and initiating a change in the binding of the NHR to other proteins, usually a second transcriptional co-activator. Generally, agonists will provide for recruitment of a second component, namely a coactivator peptide or another protein member of the transcription factor, e.g., a second NHR to form a homodimer or a different protein to form a heterodimer or binding of the agonist can release a co-repressor that is bound to the NHR. Alternatively, an antagonist will recruit a corepressor to the NHR to inhibit initiation of transcription, block binding of the agonist to the NHR or alter the dissociation of the corepressor. Candidate compounds are screened using enzyme fragment complementation as the system for detection. Genetic constructs are prepared encoding for fusion proteins under the regulatory control of transcriptional and translational genetic signals for expression of the fusion protein in a mammalian host cell. The cells are grown to a predetermined density with expression of the fusion proteins and then used in an assay medium with the candidate ligand. The turnover of the substrate by the functional enzyme resulting from the complexing of the fragments is determined optically. Further description of NHRs and their binding partners may be found at the dissertation, "Regulation of Nuclear Hormone Receptors by Corepressors and Coactivators: a Dissertation," Xiaoyang Wu, University of Massachusetts Medical School, available on the internet at hypertext transfer protocol colon slash slash escholarship.umassmed. edu/gsbs_diss/106/, which is hereby incorporated by reference in its entirety. The genetic constructs are a first construct that fuses the NHR of interest to one of the fragments of β-galactosidase, conveniently the small fragment of β-galactosidase ("ED", referred to as "PK" when a low affinity mutant of ED is employed). One may therefore have the wild-type sequence of the bacterial β-galactosidase, e.g., E. coli, or the enzyme from a different source or a functional mutant of the wild-type sequence. There are two possibilities: a short small fragment that weakly binds to the large fragment of β-galactosidase or a mutant that weakly binds to the large fragment of β-galactosidase; or longer small fragment that has a much higher affinity for the large fragment than the short small fragment. A mutant ED fragment referred to as PK has the point mutation H31R and is of 42 amino acids. By weakly binding is intended that when ED is co-expressed with the large fragment of β-galactosidase ("EA") under assay conditions, the activity will be less than about 50% of the activity with a long small fragment of at least about 90 amino acids of the N-terminal portion of β-galactosidase in the absence of protein-protein interaction.

The second construct is a fusion protein of the large β-galactosidase fragment ("EA") and a second component of the transcription factor that is recruited upon binding of a ligand. Conveniently, a steroid receptor coactivator/corepressor, usually coactivator, can be employed. Alternatively, one may use another polypeptide, such as a heat shock protein or the other member of the NHR dimer, which may include the NHR AF1 or a different protein, such as AF2, RXR, etc.

Either a short small fragment of about 36 to 60, usually 36 to 50 and more usually 36 to 45 amino acids of the N-proximal portion of β-galactosidase or a longer small fragment of at least 50, more usually at least about 60, and not more than about 110, usually not more than about 100 amino acids of the N-proximal portion of β-galactosidase is used. The short small fragment (or mutant) is desirable in providing lower background, but also results in lower signal. However, the background signal to noise ratio is usually better than the results with the long short fragment. The long short fragment is useful when the binding of the SRC to the NHR is weak, since the long short fragment has a higher affinity for the EA than the mutant ED and the overall binding between the two constructs will be increased. For the most part, the short small (mutant) fragment will be preferred.

Any NHR may be assayed whether located in the cytosol, nucleus or both. Until the NHR is activated it will not alter its association with the coactivator/corepressor to provide for formation of a functional β-galactosidase. NHRs include estrogen receptor-α and –β, progesterone receptor-α and -β, glucocorticoid receptor, mineralocorticoid receptor, thyroid hormone receptor-α and -β; retinoic acid receptor-α, -β and -γ; peroxisome proliferator-activated receptor-α, -β/δ, and γ; Rev-ErbAα and -β; RAR-related orphan receptor-α, -β and -γ; liver X receptor-α, and -β; farnesoid X receptor; vitamin D receptor; pregnane X receptor; constitutive androstane receptor; etc. Further descriptions of NHRs may be found for example in US 2005/0130232 A1, US 2004/0132038 A1, etc., which are hereby incorporated by reference in their entirety. NHR sequences may be found in NuReBase or at NUR-SA.org. Standard designations are used herein. For example, RARα is designated by the official symbol RARA; RARβ is designated by the official symbol RARβ; ERR α is designated by the official symbol ESRA; THRα is designated by the official symbol THRA; THRβ is designated by the official symbol THRB; PPARγ is designated by the official symbol PPARG; Retinoid X receptor γ (RXR) is designated by the official symbol RXRG; ESR1a designates Estrogen receptor (ESR1); ERa designates the a isoform and ERb the b isoform of the estrogen receptor; PRa designates progesterone receptor (Pgr) α; PRb designates progesterone receptor (Pgr) β; NURR1 designates Nur-related protein 1; PPARa designates peroxisome proliferator activated receptor alpha, PPARd designates peroxisome proliferator activated receptor delta; LXRa, and LXRb designate oxysterol receptor α and β, respectively.

All information on accessing and installing NUREBASE may be found at world wide web ens-lyon.fr/LBMC/laudet/nurebase/nurebase.html.

Illustrative of fusion of the small fragment of β-galactosidase, see, for example, U.S. Pat. No. 7,135,325, hereby incorporated by reference in its entirety.

The small fragment may be linked directly to a terminus, usually the N-terminus of the protein, or may be linked by up to about 20 amino acids. The amino acids for the linking group will be chosen to be non-interfering and will be primarily a matter of convenience, for example, in constructing the genetic sequence.

The large fragment will be fused to the other binding component of the NHR complex, usually at the N-terminus, conveniently the steroid receptor coactivator/corepressor, usually a coactivator (exemplified as "SRC"), or the other protein that forms the dimer. Known coactivators include C2-2, (see Thompson US 2003/0039980, hereby incorporated by reference in its entirety), TERHKILHRLLQEGST (SEQ ID NO:1), GPQTPQAQQKSLLQQLLTE (SEQ ID NO:2), TRAP220 (Thyroid Hormone Receptor-associated Protein, see J Biol Chem, Vol. 274, Issue 10, 6667-6677, Mar. 5, 1999, hereby incorporated by reference), NTKNHPMLMNLLKD-NPAQD (SEQ ID NO:3), d-22, LPYEGSLLLKLL-RAPVEEV (SEQ ID NO:4), EAEEPSLLKKLLAPANTQ (SEQ ID NO:5), and pgc1-α. In addition to the SRC (coactivator) there will also be nuclear localization and nuclear retention signals, so that the EA resides in the nucleus. Agonist binding to the first fusion protein will result in binding of the SRC to the NHR and concomitant complex formation to produce a functional β-galactosidase enzyme. Alternatively, antagonist binding will result in the recruitment of a corepressor or blockade of agonist binding.

For the preparation of the fusion protein and its expression construct, conventional splicing and insertion techniques are employed. The ED (PK) will usually be joined at its C-terminus. The ED (PK) will come from the N-terminus proximal region of the β-galactosidase enzyme.

The fusion proteins provide a functional protein that is soluble, does not aggregate so as to be unavailable for complexing, has substantially the natural folding, so as to be susceptible to binding to endogenous proteins that normally complex to the polypeptide fused to the ED, and will usually be able to perform substantially the same functions that such polypeptide performs. Therefore, the polypeptide is capable of acting as a surrogate for the natural protein to allow for measurements that are predictive of the activity of the natural protein.

The ED may be joined to the coding region in a variety of ways. For a cDNA gene, one may select a suitable restriction site for insertion of the sequence, where by using overhangs at the restriction site, the orientation is provided in the correct direction.

Various conventional ways for inserting encoding sequences into a gene can be employed. For expression constructs and decryptions of other conventional manipulative processes, See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins EDs. (1985)]; "Transcription And Translation" [B. D. Hames & S. J. Higgins, EDs. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984), which are incorporated by reference herein.

Transformed cells are cloned that have various expression levels of the two fusion proteins. The best clone is then commonly chosen by lowest $EC_{50}$ and best signal to background ratio. The cells are transformed by conventional methods. Methods include transfection, electroporation, microinjection, transduction, cell fusion, DEAE dextran, calcium phosphate precipitation, lipofection (lysosome fusion), use of a gene gun, using a viral vector, use of a carrier molecule, with a DNA vector transporter, and the like. For permanent insertion into the genome, various techniques are available for the insertion of the sequence in a homologous or non-homologous fashion. These techniques are well known. For random insertion, the introduction of the nucleic acid by any of the above methods will usually be sufficient. For homologous recombination, see, for example, U.S. Pat. Nos. 7,361,641, 5,578,461, 5,272,071 and PCT/US92/09627, incorporated by reference in their entirety and references cited therein, also hereby incorporated by reference.

Any eukaryotic cell may be employed, for the most part cell lines being employed. The cell lines will usually be mammalian, but for some purposes unicellular organisms or cells from non-vertebrates can be used. Mammalian cell lines include CHO, HeLa, HT1080, U2OS, MMTV, HepG2, HEK, and the like. Various vectors that are commercially available can be used successfully to introduce the two expression constructs into the eukaryotic cell. For an extensive description of cell lines, vectors, methods of genetic modification, and expression constructs, see published U.S. patent application serial no. 2003/0092070, Zhao, et al., May 15, 2003, paragraphs 00046-00066, which are specifically incorporated herein by reference.

Regulatory regions that may be used will be functional in the cell and may be obtained from cellular or viral genes. Illustrative regulatory regions include many promoters that are commercially available today. Expression of the fusion protein may be controlled by any promoter/enhancer element known in the art, but these regulatory elements must be functional in the host or host cell selected for expression. Promoters which may be used to control fusion gene expression include, but are not limited to, the SV40 early promoter region (Benoist and Chambon, 1981, *Nature*, 290:304-310), the promoter contained in the 3' long terminal repeat of Rous sarcoma virus (Yamamoto, et al., 1980, Cell, 22:787-797), the herpes thymidine kinase promoter (Wagner et al., 1981, *Proc. Natl. Acad. Sci. U.S.A.*, 78:1441-1445), the regulatory sequences of the metallothionein gene (Brinster et al., 1982, *Nature*, 296:39-42), etc., all incorporated herein by reference.

The screening method involves growing the cells in an appropriate medium and then washing the cells with an appropriate buffered aqueous solution, e.g., PBS, to remove any hormones. The cells are then incubated in low serum or serum-free medium, usually at least about 12 h, preferably at least about 24 h, where shorter times appear to degrade performance in some cases. Following the incubation, the cells are seeded in a medium in an appropriate environment in a small volume, followed by providing the desired stimulus, e.g., candidate compound, to provide the assay sample. The volume will generally not exceed about 250 µl, usually not more than about 200 µl, and generally be at least about 10 µl, more usually at least about 20 µl, where the volume of the candidate compound solution addition will generally dilute the cell medium less than about 1:1, usually not more than about 0.5:1. When the reagent is dry, there will be no dilution. After incubating the assay sample for sufficient time for the event of interest to occur, generally from about 1 h to about 0.5 day, a reagent solution for lysis of the cells and containing a detectable β-galactosidase substrate is added to the assay sample and one or more readings taken of the product from the substrate. The ratio of dilution will be not more than about 1:2, usually in the ratio of about 1:0.25 to 1:2, more usually 1:1 and as little at 1:0.25 or less. This dilution factor allows for reduced formation of complex during the reading period, while allowing for a robust signal, providing at least a three-fold, usually at least a 10-fold of ratio of signal to background during the period of the reading. One or more readings will be taken within 150 min, more usually within 120 min, preferably within about 60 min, and usually after about 10 min, more usually after about 15 min.

The primary interest is binding of the NHR to a second component, e.g., the coactivator/corepressor, involved in the ability of the NHR to initiate transcription. In this assay, little, if any, formation of the active enzyme occurs without there being binding of the two fusion proteins. The ultimate goal is to find ligands that can modulate cell metabolism/function through binding to the NHR.

The transformed cells to be used in the assay will be treated conventionally, generally being grown in a complete medium, washed twice with PBS and then incubated in serum-free medium overnight. The media will be conventional for the particular cells used; F-12 for CHO cells, modified Eagle's media for U20S cells, standard DMEM for HEK cells etc. The cells are then seeded in media containing fetal calf serum, conveniently media treated with charcoal/dextran to remove steroids that may be present in the fetal calf serum. The cells for use in the assay will be grown in accordance with the nature of the cells. For the most part, cells will be grown in wells in microtiter plates, the number of wells generally ranging from about 96 to 3456, generally being from 96 to 384 wells, or analyzed in suspension using capillary flow or flow cytometry, or they will be analyzed optically. The bottom will generally be clear, so that readings may be taken from the bottom of the wells, however opaque plates with instruments reading from the top can be used. The number of cells plated in a well will generally range from about $10^2$ to $10^4$ cells. The volume of the medium will usually be in the range of about 10 to 200 µl. The cells are then allowed to adhere overnight using conventional conditions of 37° C./5% $CO_2$.

After sufficient time for the stimulation of the cells to take effect from the candidate ligand and the NHR protein, substrate is provided and the turnover of the substrate is determined, where the substrate provides a detectable product. If a substrate that can permeate the cell membrane and produce a product that is not leaky, a reagent solution is added for permeabilization or lysis of the cells. It is found that the formed enzyme complex is retained, the potential for new complex to form as a result of the permeabilizing of the cells is inhibited and the background from other than complex formed from the complexing of the fusion proteins as a result of binding of the second protein is minimal. In this way a robust response to the activity of the stimulation is achieved. No further additions are required. A conventional commercially available luminescent plate reader can be used effectively. The second protein component may be a kinase, preferably a protein kinase, such as protein kinase C. The protein kinase C family is further described in Science 1 Jul. 1988: Vol. 241. no. 4861, pp. 42-52 and incorporated herein by reference for further description of the kinase family.

The reagent solution provides for lysis of the cells and exposure of any complex formed in the nucleus to the assay medium. Any conventional lysis buffer may be employed that does not interfere with the β-galactosidase reaction with its substrate. Various ionic buffers, such as CHAPS, may be employed at 1-5%, generally not more than 3%, in a convenient buffer, such as PBS or HEPES, where numerous other substitutes are known in the field.

Also present will be a β-galactosidase substrate, desirably a luminescent reagent and optionally a signal enhancer. The luminescent reagent will be in large excess in relation to the maximum amount of β-galactosidase that is likely to be formed. Conveniently, a luminescent substrate is used, available as Galacton Star from ABI in conjunction with the Emerald II enhancer. Any equivalent luminescent or fluorescent substrate composition may be employed. The substrate will be present in about 1 to 10 weight percent, while the enhancer will be present in about 10 to 30 weight percent of the reagent solution. These amounts will vary depending upon the particular substrate composition employed. The reagent solution may be prepared as a 5-20× concentrate or higher for sale or the solids may be provided as powders and dissolved in water at the appropriate proportions.

Standards will usually be used, whereby the signal is related to the concentration of a known stimulator performed under the same conditions as the candidate compound. A graph can be prepared that shows the change in signal with the change in concentration of the standard compound. The assay is sensitive to $EC_{50}$ s of not greater than 50 micromolar of candidate compound, generally sensitive to less than about 1 μM, in most cases sensitive to less than about 500 nM, frequently sensitive to less than 100 nM and can in many cases detect $EC_{50}$ values of less than 5 nM. The S/B (signal/background) ratios are generally are at least about 3 fold and can be greater than about 50 fold.

For convenience kits can be provided. In the subject assays, the EA fusion protein may be provided as a construct for expression of EA to be introduced into the cell or cells may be provided that are appropriately modified to provide EA in the cell. Generally, the kits would include an insert with instructions for performing the assay. The instructions may be printed or electronic, e.g., a CD or floppy disk. The kits find use in marketing the product and encouraging the use of the assay for research and commercial settings.

The following examples are offered by way of illustration and not by way of limitation.

EXPERIMENTAL

The following is the full sequence (SEQ ID NO:6) for the plasmid introduced into the CHO cells for expression of the TRAP-220-EA-Nuc fusion protein.

```
   1 ACTAGTTAGC TAACTAGCTC TGTATCTGGC GGACCCGTGG TGGAACTGAC
  51 GAGTTCTGAA CACCCGGCCG CAACCCTGGG AGACGTCCCA GGGACTTTGG
 101 GGGCCGTTTT TGTGGCCCGA CCTGAGGAAG GGAGTCGATG TGGAATCCGA
 151 CCCCGTCAGG ATATGTGGTT CTGGTAGGAG ACGAGAACCT AAAACAGTTC
 201 CCGCCTCCGT CTGAATTTTT GCTTTCGGTT TGGAACCGAA GCCGCGCGTC
 251 TTGTCTGCTG CAGCGCTGCA GCATCGTTCT GTGTTGTCTC TGTCTGACTG
 301 TGTTTCTGTA TTTGTCTGAA AATTAGGGCC AGACTGTTAC CACTCCCTTA
 351 AGTTTGACCT TAGGTCACTG GAAAGATGTC GAGCGGATCG CTCACAACCA
 401 GTCGGTAGAT GTCAAGAAGA GACGTTGGGT TACCTTCTGC TCTGCAGAAT
 451 GGCCAACCTT TAACGTCGGA TGGCCGCGAG ACGGCACCTT TAACCGAGAC
 501 CTCATCACCC AGGTTAAGAT CAAGGTCTTT TCACCTGGCC CGCATGGACA
 551 CCCAGACCAG GTCCCCTACA TCGTGACCTG GGAAGCCTTG GCTTTTGACC
 601 CCCCTCCCTG GGTCAAGCCC TTTGTACACC CTAAGCCTCC GCCTCCTCTT
 651 CCTCCATCCG CCCCGTCTCT CCCCCTTGAA CCTCCTCGTT CGACCCCGCC
 701 TCGATCCTCC CTTTATCCAG CCCTCACTCC TTCTCTAGGC GCCGGAATTC
 751 CGATCTGATC AGCTTGCCAC AACCCGTACC AAAGATGGAT AGATCCGGAA
 801 AGCCTGAACT CACCGCGACG TCTGTCGAGA AGTTTCTGAT CGAAAAGTTC
 851 GACAGCGTCT CCGACCTGAT GCAGCTCTCG GAGGGCGAAG AATCTCGTGC
 901 TTTCAGCTTC GATGTAGGAG GGCGTGGATA TGTCCTGCGG GTAAATAGCT
 951 GCGCCGATGG TTTCTACAAA GATCGTTATG TTTATCGGCA CTTTGCATCG
1001 GCCGCGCTCC CGATTCCGGA AGTGCTTGAC ATTGGGGAAT TCAGCGAGAG
1051 CCTGACCTAT TGCATCTCCC GCCGTGCACA GGGTGTCACG TTGCAAGACC
1101 TGCCTGAAAC CGAACTGCCC GCTGTTCTGC AGCCGGTCGC GGAGGCCATG
1151 GATGCGATCG CTGCGGCCGA TCTTAGCCAG ACGAGCGGGT TCGGCCCATT
1201 CGGACCGCAA GGAATCGGTC AATACACTAC ATGGCGTGAT TTCATATGCG
1251 CGATTGCTGA TCCCCATGTG TATCACTGGC AAACTGTGAT GGACGACACC
1301 GTCAGTGCGT CCGTCGCGCA GGCTCTCGAT GAGCTGATGC TTTGGGCCGA
1351 GGACTGCCCC GAAGTCCGGC ACCTCGTGCA CGCGGATTTC GGCTCCAACA
```

```
-continued
1401 ATGTCCTGAC GGACAATGGC CGCATAACAG CGGTCATTGA CTGGAGCGAG
1451 GCGATGTTCG GGGATTCCCA ATACGAGGTC GCCAACATCT TCTTCTGGAG
1501 GCCGTGGTTG GCTTGTATGG AGCAGCAGAC GCGCTACTTC GAGCGGAGGC
1551 ATCCGGAGCT TGCAGGATCG CCGCGGCTCC GGGCGTATAT GCTCCGCATT
1601 GGTCTTGACC AACTCTATCA GAGCTTGGTT GACGGCAATT TCGATGATGC
1651 AGCTTGGGCG CAGGGTCGAT GCGACGCAAT CGTCCGATCC GGAGCCGGGA
1701 CTGTCGGGCG TACACAAATC GCCCGCAGAA GCGCGGCCGT CTGGACCGAT
1751 GGCTGTGTAG AAGTACTCGC CGATAGTGGA AACCGACGCC CCAGCACTCG
1801 TCCGAGGGCA AAGGAATAGA GTAGATGCCG ACCGAACAAG AGCTGATTTC
1851 GAGAACGCCT CAGCCAGCAA CTCGCGCGAG CCTAGCAAGG CAAATGCGAG
1901 AGAACGGCCT TACGCTTGGT GGCACAGTTC TCGTCCACAG TTCGCTAAGC
1951 TCGCTCGGCT GGGTCGCGGG AGGGCCGGTC GCAGTGATTC AGGCCCTTCT
2001 GGATTGTGTT GGTCCCCAGG GCACGATTGT CATGCCCACG CACTCGGGTG
2051 ATCTGACTGA TCCCGCAGAT TGGAGATCGC CGCCCGTGCC TGCCGATTGG
2101 GTGCAGATCT AGAGCTCGCT GATCCGGCCA TTAGCCATAT TATTCATTGG
2151 TTATATAGCA TAAATCAATA TTGGCTATTG GCCATTGCAT ACGTTGTATC
2201 CATATCATAA TATGTACATT TATATTGGCT CATGTCCAAC ATTACCGCCA
2251 TGTTGACATT GATTATTGAC TAGTTATTAA TAGTAATCAA TTACGGGGTC
2301 ATTAGTTCAT AGCCCATATA TGGAGTTCCG CGTTACATAA CTTACGGTAA
2351 ATGGCCCGCC TGGCTGACCG CCCAACGACC CCCGCCCATT GACGTCAATA
2401 ATGACGTATG TTCCCATAGT AACGCCAATA GGGACTTTCC ATTGACGTCA
2451 ATGGGTGGAG TATTTACGGT AAACTGCCCA CTTGGCAGTA CATCAAGTGT
2501 ATCATATGCC AAGTACGCCC CCTATTGACG TCAATGACGG TAAATGGCCC
2551 GCCTGGCATT ATGCCCAGTA CATGACCTTA TGGGACTTTC CTACTTGGCA
2601 GTACATCTAC GTATTAGTCA TCGCTATTAC CATGGTGATG CGGTTTTGGC
2651 AGTACATCAA TGGGCGTGGA TAGCGGTTTG ACTCACGGGG ATTTCCAAGT
2701 CTCCACCCCA TTGACGTCAA TGGGAGTTTG TTTTGGCACC AAAATCAACG
2751 GGACTTTCCA AAATGTCGTA ACAACTCCGC CCCATTGACG CAAATGGGCG
2801 GTAGGCGTGT ACGGTGGGAG GTCTATATAA GCAGAGCTCT CTGGCTAACT
2851 AGAGAACCCA CTGCTTACTG GCTTATCGAA ATTAATACGA CTCACTATAG
2901 GGAGACCCAA GCTGGCTAGC ACCATGCATA ACACAAAGAA TCACCCTATG
2951 CTCATGAACC TGCTGAAGGA CAATCCTGCC CAGGACACCG GTTCAAAGCT
3001 TGGTACCATG GATCCTCGCG CCTCCTCCAA TTCACTGGCC GTCGTTTTAC
3051 AAGAGGCCCG CACCGATCGC CCTTCCCAAC AGTTGCGCAG CCTGAATGGC
3101 GAATGGCGCT TTGCCTGGTT TCCGGCACCA GAAGCGGTGC CGGAAAGCTG
3151 GCTGGAGTGC GATCTTCCTG AGGCCGATAC TGTCGTCGTC CCCTCAAACT
3201 GGCAGATGCA CGGTTACGAT GCGCCCATCT ACACCAACGT GACCTATCCC
3251 ATTACGGTCA ATCCGCCGTT TGTTCCCACG GAGAATCCGA CGGGTTGTTA
3301 CTCGCTCACA TTTAATGTTG ATGAAAGCTG GCTACAGGAA GGCCAGACGC
3351 GAATTATTTT TGATGGCGTT AACTCGGCGT TTCATCTGTG GTGCAACGGG
3401 CGCTGGGTCG GTTACGGCCA GGACAGTCGT TTGCCGTCTG AATTTGACCT
```

-continued

```
3451 GAGCGCATTT TTACGCGCCG GAGAAAACCG CCTCGCGGTG ATGGTGCTGC
3501 GCTGGAGTGA CGGCAGTTAT CTGGAAGATC AGGATATGTG GCGGATGAGC
3551 GGCATTTTCC GTGACGTCTC GTTGCTGCAT AAACCGACTA CACAAATCAG
3601 CGATTTCCAT GTTGCCACTC GCTTTAATGA TGATTTCAGC CGCGCTGTAC
3651 TGGAGGCTGA AGTTCAGATG TGCGGCGAGT TGCGTGACTA CCTACGGGTA
3701 ACAGTTTCTT TATGGCAGGG TGAAACGCAG GTCGCCAGCG GCACCGCGCC
3751 TTTCGGCGGT GAAATTATCG ATGAGCGTGG TGGTTATGCC GATCGCGTCA
3801 CACTACGTCT GAACGTCGAA AACCCGAAAC TGTGGAGCGC CGAAATCCCG
3851 AATCTCTATC GTGCGGTGGT TGAACTGCAC ACCGCCGACG GCACGCTGAT
3901 TGAAGCAGAA GCCTGCGATG TCGGTTTCCG CGAGGTGCGG ATTGAAAATG
3951 GTCTGCTGCT GCTGAACGGC AAGCCGTTGC TGATTCGAGG CGTTAACCGT
4001 CACGAGCATC ATCCTCTGCA TGGTCAGGTC ATGGATGAGC AGACGATGGT
4051 GCAGGATATC CTGCTGATGA AGCAGAACAA CTTTAACGCC GTGCGCTGTT
4101 CGCATTATCC GAACCATCCG CTGTGGTACA CGCTGTGCGA CCGCTACGGC
4151 CTGTATGTGG TGGATGAAGC CAATATTGAA ACCCACGGCA TGGTGCCAAT
4201 GAATCGTCTG ACCGATGATC CGCGCTGGCT ACCGGCGATG AGCGAACGCG
4251 TAACGCGAAT GGTGCAGCGC GATCGTAATC ACCCGAGTGT GATCATCTGG
4301 TCGCTGGGGA ATGAATCAGG CCACGGCGCT AATCACGACG CGCTGTATCG
4351 CTGGATCAAA TCTGTCGATC CTTCCCGCCC GGTGCAGTAT GAAGGCGGCG
4401 GAGCCGACAC CACGGCCACC GATATTATTT GCCCGATGTA CGCGCGCGTG
4451 GATGAAGACC AGCCCTTCCC GGCTGTGCCG AAATGGTCCA TCAAAAAATG
4501 GCTTTCGCTA CCTGGAGAGA CGCGCCCGCT GATCCTTTGC GAATACGCCC
4551 ACGCGATGGG TAACAGTCTT GGCGGTTTCG CTAAATACTG GCAGGCGTTT
4601 CGTCAGTATC CCCGTTTACA GGGCGGCTTC GTCTGGGACT GGGTGGATCA
4651 GTCGCTGATT AAATATGATG AAAACGGCAA CCCGTGGTCG GCTTACGGCG
4701 GTGATTTTGG CGATACGCCG AACGATCGCC AGTTCTGTAT GAACGGTCTG
4751 GTCTTTGCCG ACCGCACGCC GCATCCAGCG CTGACGGAAG CAAAACACCA
4801 GCAGCAGTTT TTCCAGTTCC GTTTATCCGG GCAAACCATC GAAGTGACCA
4851 GCGAATACCT GTTCCGTCAT AGCGATAACG AGCTCCTGCA CTGGATGGTG
4901 GCGCTGGATG GTAAGCCGCT GGCAAGCGGT GAAGTGCCTC TGGATGTCGC
4951 TCCACAAGGT AAACAGTTGA TTGAACTGCC TGAACTACCG CAGCCGGAGA
5001 GCGCCGGGCA ACTCTGGCTC ACAGTACGCG TAGTGCAACC GAACGCGACC
5051 GCATGGTCAG AAGCCGGCCA CATCAGCGCC TGGCAGCAGT GGCGTCTGGC
5101 GGAAAACCTC AGTGTGACGC TCCCCGCCGC GTCCCACGCC ATCCCGCATC
5151 TGACCACCAG CGAAATGGAT TTTTGCATCA AGCTGGGTAA TAAGCGTTGG
5201 CAATTTAACC GCCAGTCAGG CTTTCTTTCA CAGATGTGGA TTGGCGATAA
5251 AAAACAACTG CTGACGCCGC TGCGCGATCA GTTCACCCGT GCACCGCTGG
5301 ATAACGACAT TGGCGTAAGT GAAGCGACCC GCATTGACCC TAACGCCTGG
5351 GTCGAACGCT GGAAGGCGGC GGGCCATTAC CAGGCCGAAG CAGCGTTGTT
5401 GCAGTGCACG GCAGATACAC TTGCTGACGC GGTGCTGATT ACGACCGCTC
5451 ACGCGTGGCA GCATCAGGGG AAAACCTTAT TTATCAGCCG GAAAACCTAC
```

-continued

```
5501 CGGATTGATG GTAGTGGTCA AATGGCGATT ACCGTTGATG TTGAAGTGGC
5551 GAGCGATACA CCGCATCCGG CGCGGATTGG CCTGAACTGC CAGCTGGCGC
5601 AGGTAGCAGA GCGGGTAAAC TGGCTCGGAT TAGGGCCGCA AGAAAACTAT
5651 CCCGACCGCC TTACTGCCGC CTGTTTTGAC CGCTGGGATC TGCCATTGTC
5701 AGACATGTAT ACCCCGTACG TCTTCCCGAG CGAAAACGGT CTGCGCTGCG
5751 GGACGCGCGA ATTGAATTAT GGCCCACACC AGTGGCGCGG CGACTTCCAG
5801 TTCAACATCA GCCGCTACAG TCAACAGCAA CTGATGGAAA CCAGCCATCG
5851 CCATCTGCTG CACGCGGAAG AAGGCACATG GCTGAATATC GACGGTTTCC
5901 ATATGGGGAT TGGTGGAGAC GACTCCTGGA GCCCGTCAGT ATCGGCGGAA
5951 TTACAGCTGA GCGCCGGTCG CTACCATTAC CAGTTGGTCT GGTGTCAAAA
6001 AGCGGCCGCA GATCCAAAAA AGAAGAGAAA GGTAGATCCA AAAAGAAGA
6051 GAAAGGTAGA TCCAAAAAAG AAGAGAAAGG TAGATACGGC CCTCGAGCCT
6101 CCCCCAGTGT CCAAGAGGGA ATCCAAATCC AGGTCGCGAT CGAAGAGTCC
6151 CCCCAAGTCT CCTGAAGAGG AAGGAGCGGT GTCCTCTTCT AGGGGTCTTT
6201 CCCCTCTCGC CAAAGGAATG CAAGGTCTGT TGAATGTCGT GAAGGAAGCA
6251 GTTCCTCTGG AAGCTTCTTG AAGACAAACA ACGTCTGTAG CGACCCTTTG
6301 CAGGCAGCGG AACCCCCAC CTGGCGACAG GTGCCTCTGC GGCCAAAAGC
6351 CACCCTTAAT GGCCTAACAT CGATAAAATA AAAGATTTTA TTTAGTCTCC
6401 AGAAAAAGGG GGGAATGAAA GACCCCACCT GTAGGTTTGG CAAGCTAGCT
6451 TAAGTAACGC CATTTTGCAA GGCATGGAAA ATACATAAC TGAGAATAGA
6501 GAAGTTCAGA TCAAGGTCAG GAACAGATGG AACAGCTGAA TATGGGCCAA
6551 ACAGGATATC TGTGGTAAGC AGTTCCTGCC CCGGCTCAGG GCCAAGAACA
6601 GATGGAACAG CTGAATATGG GCCAAACAGG ATATCTGTGG TAAGCAGTTC
6651 CTGCCCCGGC TCAGGGCCAA GAACAGATGG TCCCCAGATG CGGTCCAGCC
6701 CTCAGCAGTT TCTAGAGAAC CATCAGATGT TTCCAGGGTG CCCCAAGGAC
6751 CTGAAATGAC CCTGTGCCTT ATTTGAACTA ACCAATCAGT TCGCTTCTCG
6801 CTTCTGTTCG CGCGCTTCTG CTCCCCGAGC TCAATAAAAG AGCCCACAAC
6851 CCCTCACTCG GGGCGCCAGT CCTCCGATTG ACTGAGTCGC CCGGGTACCC
6901 GTGTATCCAA TAAACCCTCT TGCAGTTGCA TCCGACTTGT GGTCTCGCTG
6951 TTCCTTGGGA GGGTCTCCTC TGAGTGATTG ACTACCCGTC AGCGGGGGTC
7001 TTTCATTTGG GGGCTCGTCC GGGATCGGGA GACCCCTGCC CAGGGACCAC
7051 CGACCCACCA CCGGGAGGTA AGCTGGCTGC CTCGCGCGTT TCGGTGATGA
7101 CGGTGAAAAC CTCTGACACA TGCAGCTCCC GGAGACGGTC ACAGCTTGTC
7151 TGTAAGCGGA TGCCGGGAGC AGACAAGCCC GTCAGGGCGC GTCAGCGGGT
7201 GTTGGCGGGT GTCGGGGCGC AGCCATGACC CAGTCACGTA GCGATAGCGG
7251 AGTGTATACT GGCTTAACTA TGCGGCATCA GAGCAGATTG TACTGAGAGT
7301 GCACCATATG CGGTGTGAAA TACCGCACAG ATGCGTAAGG AGAAAATACC
7351 GCATCAGGCG CTCTTCCGCT TCCTCGCTCA CTGACTCGCT GCGCTCGGTC
7401 GTTCGGCTGC GGCGAGCGGT ATCAGCTCAC TCAAAGGCGG TAATACGGTT
7451 ATCCACAGAA TCAGGGGATA ACGCAGGAAA GAACATGTGA GCAAAAGGCC
7501 AGCAAAAGGC CAGGAACCGT AAAAAGGCCG CGTTGCTGGC GTTTTTCCAT
```

-continued

```
7551 AGGCTCCGCC CCCCTGACGA GCATCACAAA AATCGACGCT CAAGTCAGAG

7601 GTGGCGAAAC CCGACAGGAC TATAAAGATA CCAGGCGTTT CCCCCTGGAA

7651 GCTCCCTCGT GCGCTCTCCT GTTCCGACCC TGCCGCTTAC CGGATACCTG

7701 TCCGCCTTTC TCCCTTCGGG AAGCGTGGCG CTTTCTCATA GCTCACGCTG

7751 TAGGTATCTC AGTTCGGTGT AGGTCGTTCG CTCCAAGCTG GGCTGTGTGC

7801 ACGAACCCCC CGTTCAGCCC GACCGCTGCG CCTTATCCGG TAACTATCGT

7851 CTTGAGTCCA ACCCGGTAAG ACACGACTTA TCGCCACTGG CAGCAGCCAC

7901 TGGTAACAGG ATTAGCAGAG CGAGGTATGT AGGCGGTGCT ACAGAGTTCT

7951 TGAAGTGGTG GCCTAACTAC GGCTACACTA GAAGGACAGT ATTTGGTATC

8001 TGCGCTCTGC TGAAGCCAGT TACCTTCGGA AAAAGAGTTG GTAGCTCTTG

8051 ATCCGGCAAA CAAACCACCG CTGGTAGCGG TGGTTTTTTT GTTTGCAAGC

8101 AGCAGATTAC GCGCAGAAAA AAAGGATCTC AAGAAGATCC TTTGATCTTT

8151 TCTACGGGGT CTGACGCTCA GTGGAACGAA AACTCACGTT AAGGGATTTT

8201 GGTCATGAGA TTATCAAAAA GGATCTTCAC CTAGATCCTT TTAAATTAAA

8251 AATGAAGTTT TAAATCAATC TAAAGTATAT ATGAGTAAAC TTGGTCTGAC

8301 AGTTACCAAT GCTTAATCAG TGAGGCACCT ATCTCAGCGA TCTGTCTATT

8351 TCGTTCATCC ATAGTTGCCT GACTCCCCGT CGTGTAGATA ACTACGATAC

8401 GGGAGGGCTT ACCATCTGGC CCCAGTGCTG CAATGATACC GCGAGACCCA

8451 CGCTCACCGG CTCCAGATTT ATCAGCAATA AACCAGCCAG CCGGAAGGGC

8501 CGAGCGCAGA AGTGGTCCTG CAACTTTATC CGCCTCCATC CAGTCTATTA

8551 ATTGTTGCCG GGAAGCTAGA GTAAGTAGTT CGCCAGTTAA TAGTTTGCGC

8601 AACGTTGTTG CCATTGCTGC AGGCATCGTG GTGTCACGCT CGTCGTTTGG

8651 TATGGCTTCA TTCAGCTCCG GTTCCCAACG ATCAAGGCGA GTTACATGAT

8701 CCCCCATGTT GTGCAAAAAA GCGGTTAGCT CCTTCGGTCC TCCGATCGTT

8751 GTCAGAAGTA AGTTGGCCGC AGTGTTATCA CTCATGGTTA TGGCAGCACT

8801 GCATAATTCT CTTACTGTCA TGCCATCCGT AAGATGCTTT TCTGTGACTG

8851 GTGAGTACTC AACCAAGTCA TTCTGAGAAT AGTGTATGCG GCGACCGAGT

8901 TGCTCTTGCC CGGCGTCAAC ACGGGATAAT ACCGCGCCAC ATAGCAGAAC

8951 TTTAAAAGTG CTCATCATTG GAAAACGTTC TTCGGGGCGA AAACTCTCAA

9001 GGATCTTACC GCTGTTGAGA TCCAGTTCGA TGTAACCCAC TCGTGCACCC

9051 AACTGATCTT CAGCATCTTT TACTTTCACC AGCGTTTCTG GGTGAGCAAA

9101 AACAGGAAGG CAAAATGCCG CAAAAAAGGG AATAAGGGCG ACACGGAAAT

9151 GTTGAATACT CATACTCTTC CTTTTTCAAT ATTATTGAAG CATTTATCAG

9201 GGTTATTGTC TCATGAGCGG ATACATATTT GAATGTATTT AGAAAAATAA

9251 ACAAATAGGG GTTCCGCGCA CATTTCCCCG AAAAGTGCCA CCTGACGTCT

9301 AAGAAACCAT TATTATCATG ACATTAACCT ATAAAAATAG GCGTATCACG

9351 AGGCCCTTTC GTCTTCAAGA ATTCATACCA GATCACCGAA AACTGTCCTC

9401 CAAATGTGTC CCCCTCACAC TCCCAAATTC GCGGGCTTCT GCCTCTTAGA

9451 CCACTCTACC CTATTCCCCA CACTCACCGG AGCCAAAGCC GCGGCCCTTC

9501 CGTTTCTTTG CTTTTGAAAG ACCCCACCCG TAGGTGGCAA GCTAGCTTAA

9551 GTAACGCCAC TTTGCAAGGC ATGGAAAAAT ACATAACTGA GAATAGAAAA
```

-continued

```
9601   GTTCAGATCA AGGTCAGGAA CAAAGAAACA GCTGAATACC AAACAGGATA
9651   TCTGTGGTAA GCGGTTCCTG CCCCGGCTCA GGGCCAAGAA CAGATGAGAC
9701   AGCTGAGTGA TGGGCCAAAC AGGATATCTG TGGTAAGCAG TTCCTGCCCC
9751   GGCTCGGGGC CAAGAACAGA TGGTCCCCAG ATGCGGTCCA GCCCTCAGCA
9801   GTTTCTAGTG AATCATCAGA TGTTTCCAGG GTGCCCCAAG GACCTGAAAA
9851   TGACCCTGTA CCTTATTTGA ACTAACCAAT CAGTTCGCTT CTCGCTTCTG
9901   TTCGCGCGCT TCCGCTCTCC GAGCTCAATA AAAGAGCCCA CAACCCCTCA
9951   CTCGGCGCGC CAGTCTTCCG ATAGACTGCG TCGCCCGGGT ACCCGTATTC
10001  CCAATAAAGC CTCTTGCTGT TTGCATCCGA ATCGTGGTCT CGCTGTTCCT
10051  TGGGAGGGTC TCCTCTGAGT GATTGACTAC CCACGACGGG GGTCTTTCAT
10101  TTGGGGGCTC GTCCGGGATT TGGAGACCCC TGCCCAGGGA CCACCGACCC
10151  ACCACCGGGA GGTAAGCTGG CCAGCAACTT ATCTGTGTCT GTCCGATTGT
10201  CTAGTGTCTA TGTTTGATGT TATGCGCCTG CGTCTGT.
```

The genes for the NHRs may be obtained from any convenient source: commercial supplier; RT_PCR from mRNA isolated in accordance with conventional procedures using known sequences as probes; PCR from genomic DNA using primers from known sequences. The genes are PCR amplified to remove the stop codon at the 3' end. The genes are then digested with restriction enzymes where the restriction site is included with the primer sequences. These products are then purified in conventional ways and then ligated into a commercial vector into which the ED or EA has been inserted. Separating the ED and the EA from the gene is a linker that provides flexibility to the fusion proteins to enhance complementation. This linker is not required for activity. The transcriptional regulatory region is generally present in commercial vectors, such as the 5' LTR of the virus used for the vector. Alternatively, the CMV promoter may be used. The resulting vector is then introduced into the host cell by liposome mediated transfection or retroviral infection with Moloney murine leukemia virus vector and packaging cell lines. The resulting virus is then used for viral infection. The vectors also include selection genes, such as hygromycin resistance and cells into which the construct is integrated are selected in a conventional selection medium. The surviving cells are then screened in an agonist dose response assay using adherent cells and the Path-Hunter® Detection Kit reagents in white-walled microplates.

The following TABLE 1 provides exemplary protocols:

TABLE 1

| Steps | Volumes (384-well full volume) | Volumes (96-well full volume) |
| --- | --- | --- |
| Step 1: Plate Cells | Add 25 μL of cells in each well at a preferred density of 5,000-10,000 cells per well. Cells should be seeded In media* + 1.5% Charcoal/Dextran treated serum | Add 100 μL of cells in each well at a preferred density of 20,000-30,000 cells per well. Cells should be seeded in media* + 1.5% Charcoal/Dextran treated serum |
| Step 2: Treat Cells* | Dissolve compounds**, add 1-5 μl per well, and incubate for 3 hrs @ 37° C.* | Dissolve compounds, add 5-10 μl per well, and incubate for 3 hrs @ 37° C.* |
| Step 3: Add Detection Reagents | Add 12 μl of detection reagents*** per well. | Add 50 μl of detection reagents per well. |
| Step 4: Read Samples | Samples can be read on any standard luminescence plate reader after 60 minutes of incubation. | Samples can be read on any standard luminescence plate reader after 60 minutes of incubation. |

Note:
Dissolve compound according to manufacturer's instructions and without exceeding 1% organic solvent such as DMSO or EtOH in the assay medium.
CHO:
*F12 + 10% FBS, 1X P/S/G and 250 mg/mL Hygromycin and 600 mg/mL G418 Cells are maintained at ~70% confluence, passed two to three times a week.
**Candidate compound is dissolved in a minimum amount of solvent, e.g., ethanol or DMSO
***Detection reagent is prepared by combining PathHunter ™ Cell Assay Buffer (DiscoveRx, Fremont, CA), Galacton Star ® and Emerald II ® reagent to 25 μl of cells + compound at a ratio of 19:1:5.

The results of the assays are set forth in the figures and are further tabulated below in TABLE 2. All of the cells were CHO cells and were stable through 20 passages.

TABLE 2

| Figure | NHR | S/B | $EC_{50}$ nM | Ligand |
|---|---|---|---|---|
| 2 | ERRα | 3 | 300 | XCT790* |
| 3 | THRα | 78 | 15 | T3 |
| 4 | RARα | 3 | 29 | 9-cis-RA |
| 5 | RARβ | 3 | 29 | 9-cis-RA |

*CAS registry 725247-18-7

It is evident from the above results that the subject assay provides for a sensitive, accurate technique for measuring modulation of activation of NHRs in response to candidate compounds. The assay is easy to perform, using conventional equipment, can be used for rapidly screening numerous candidates for their activity and is readily adaptable to any of the known or orphan NHRs. The assay has a novel format for pathway profiling. The assays have a reduced time relative to reporter genes, there being no requirement for transcriptional activity. There is no requirement for target over expression. The method is readily adaptable to automated screening employing robotics. NHR activation is detected directly without imaging.

Although the invention has been described with reference to the above examples, it will be understood that modifications and variations are encompassed within the spirit and scope of the invention. Accordingly, the invention is limited only by the following claims. All patents and publications referred to in the specification are incorporated by reference as if fully set forth therein.

What is claimed is:

1. A method for screening a candidate compound for modulating the binding of a nuclear hormone receptor to a second protein component that binds to the nuclear hormone receptor to form a complex to initiate transcription, comprising:
   (a) using a cell in an assay medium transformed with first and second genetic constructs having regulatory sequences functional in said cell for expression of said constructs,
   (b) said method employing first and second fragments of β-galactosidase which when complexed form an active enzyme, one of said fragments being an enzyme donor ("ED") and the other of said fragments being an enzyme acceptor ("EA") that is larger than said ED,
   (c) said first genetic construct encoding a first fusion protein of a first fragment of said β-galactosidase fused to said nuclear hormone receptor to serve as a surrogate for said nuclear hormone receptor;
   (d) said second genetic construct encoding a second fusion protein of said second fragment of β-galactosidase fused to said second protein component, wherein said second protein component is selected from the group consisting of (i) coactivator, (ii) corepressor, (iii) member of a homodimer, and (iv) member of a heterodimer, of said nuclear hormone receptor;
   (e) incubating said cell in said assay medium with a candidate compound for sufficient time for any binding between said first fusion protein fused to a nuclear hormone receptor and said second fusion protein, fused to said second enzyme fragment, that binds to the nuclear hormone receptor to form a complex to initiate transcription, to occur, said binding causing formation of active β-galactosidase;
   (f) adding a β-galactosidase substrate that provides for a signal that is detectable; and
   (g) determining said signal as a measure of the modulation resulting from said binding by said candidate compound, wherein binding results in a signal and a candidate compound modulating binding modulates said signal.

2. The method according to claim 1, wherein said ED fragment is a low affinity β galactosidase fragment from about 36 to 50 amino acids long.

3. The method according to claim 1, wherein a lysing reagent is added after said incubating.

4. The method according to claim 1, wherein said ED is fused to said nuclear hormone receptor.

5. The method according to claim 1, wherein said nuclear hormone receptor is selected from the group consisting of estrogen-related receptor α (ERRα), thyroid hormone receptor α (THRα), thyroid hormone receptor β (THRβ), retinoic acid receptor α (RARα), retinoic acid receptor β (RARβ), one of peroxisome proliferator-activated receptor γ (PPARγ) or retinoid X receptor γ (RXRγ), estrogen receptor 1a (ESR1a), the a isoform of the estrogen receptor (Era), the b isoform of the estrogen receptor (ERb), progesterone receptor α (PRa), progesterone receptor β (PRb), Nur-related protein 1 (NURR1), peroxisome proliferator-activated receptor alpha (PPARa), peroxisome proliferator-activated receptor delta (PPARd), oxysterol receptor α (LXRa) and oxysterol receptor β (LXRb).

6. The method according to claim 1, wherein said cells are CHO or HepG2.

7. The method according to claim 1, wherein said determining is capable of determining an $EC_{50}$ of less than about 1 µM.

8. The method according to claim 1, wherein a ratio of said signal to background is not less than 2 fold.

9. A method for screening candidate compounds for modulating the binding of a nuclear hormone receptor to a coactivator,
(a) using a cell in an assay medium transformed with first and second genetic constructs having regulatory sequences functional in said cell for expression of said constructs,
(b) said method employing a small ("ED") and a large ("EA") fragment of β-galactosidase which when complexed form an active enzyme,
(c) said first genetic construct encoding a fusion protein of said ED fused to said nuclear hormone receptor to serve as a surrogate for said nuclear hormone receptor;
(d) said second genetic construct encoding said coactivator fused to said EA;
(e) incubating said cells in said assay medium with a candidate compound for sufficient time for any binding between said coactivator fused to said EA and said fusion protein of ED fused to said nuclear hormone receptor to occur;
(f) adding a reagent solution and substrate that provides for a detectable signal to said cells to lyse said cells; and
(g) determining said detectable signal as a measure of the modulation resulting from said binding by said candidate compound, wherein binding results in a signal and a candidate compound modulating said binding modulates said signal.

10. The method according to claim 1, wherein said nuclear hormone receptor is selected from the group consisting of ERRα, THRα, RARα and RARβ.

11. The method according to claim 1 where said second protein component is steroid receptor coactivator-1 (SRC-1) or thyroid hormone receptor-associated protein (TRAP-220).

12. The method of claim 1 wherein said second genetic construct resides in a nucleus in said cell and said binding occurs in the nucleus.

13. The method of claim 1 wherein said second genetic construct further encodes nuclear localization and nuclear retention signals, whereby said second fusion protein is localized to the cell's nucleus.

14. The method of claim 2 wherein said ED comprises not more than 100 amino acids of the N-proximal portion of β-galactosidase.

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: human

<400> SEQUENCE: 1

Thr Glu Arg His Lys Ile Leu His Arg Leu Leu Gln Glu Gly Ser Thr
1               5                   10                  15

<210> SEQ ID NO 2
<211> LENGTH: 19
<212> TYPE: PRT
<213> ORGANISM: human

<400> SEQUENCE: 2

Gly Pro Gln Thr Pro Gln Ala Gln Gln Lys Ser Leu Leu Gln Gln Leu
1               5                   10                  15

Leu Thr Glu

<210> SEQ ID NO 3
<211> LENGTH: 19
<212> TYPE: PRT
<213> ORGANISM: human

<400> SEQUENCE: 3

Asn Thr Lys Asn His Pro Met Leu Met Asn Leu Leu Lys Asp Asn Pro
1               5                   10                  15

Ala Gln Asp

<210> SEQ ID NO 4
<211> LENGTH: 19
<212> TYPE: PRT
<213> ORGANISM: human

<400> SEQUENCE: 4

Leu Pro Tyr Glu Gly Ser Leu Leu Leu Lys Leu Leu Arg Ala Pro Val
1               5                   10                  15

Glu Glu Val

<210> SEQ ID NO 5
<211> LENGTH: 18
<212> TYPE: PRT
<213> ORGANISM: human
```

<400> SEQUENCE: 5

Glu Ala Glu Glu Pro Ser Leu Leu Lys Lys Leu Leu Ala Pro Ala Asn
1               5                   10                  15

Thr Gln

<210> SEQ ID NO 6
<211> LENGTH: 10237
<212> TYPE: DNA
<213> ORGANISM: artificial
<220> FEATURE:
<223> OTHER INFORMATION: fusion protein

<400> SEQUENCE: 6

```
actagttagc taactagctc tgtatctggc ggacccgtgg tggaactgac gagttctgaa      60
cacccggccg caaccctggg agacgtccca gggactttgg gggccgtttt tgtggcccga     120
cctgaggaag ggagtcgatg tggaatccga ccccgtcagg atatgtggtt ctggtaggag     180
acgagaacct aaaacagttc ccgcctccgt ctgaattttt gctttcggtt tggaaccgaa     240
gccgcgcgtc ttgtctgctg cagcgctgca gcatcgttct gtgttgtctc tgtctgactg     300
tgtttctgta tttgtctgaa aattagggcc agactgttac cactccctta agtttgacct     360
taggtcactg gaaagatgtc gagcggatcg ctcacaacca gtcggtagat gtcaagaaga     420
gacgttgggt taccttctgc tctgcagaat ggccaacctt aacgtcggat ggccgcgag     480
acggcacctt taaccgagac ctcatcaccc aggttaagat caaggtcttt tcacctggcc     540
cgcatggaca cccagaccag gtcccctaca tcgtgacctg ggaagccttg gcttttgacc     600
cccctccctg ggtcaagccc tttgtacacc ctaagcctcc gcctcctctt cctccatccg     660
ccccgtctct cccccttgaa cctcctcgtt cgaccccgcc tcgatcctcc ctttatccag     720
ccctcactcc ttctctaggc gccggaattc cgatctgatc agcttgccac aacccgtacc     780
aaagatggat agatccggaa agcctgaact caccgcgacg tctgtcgaga gtttctgat      840
cgaaaagttc gacagcgtct ccgacctgat gcagctctcg gagggcgaag aatctcgtgc     900
tttcagcttc gatgtaggag ggcgtggata tgtcctgcgg gtaaatagct gcgccgatgg     960
tttctacaaa gatcgttatg tttatcggca ctttgcatcg gccgcgctcc cgattccgga    1020
agtgcttgac attggggaat tcagcgagag cctgacctat tgcatctccc gccgtgcaca    1080
gggtgtcacg ttgcaagacc tgcctgaaac cgaactgccc gctgttctgc agccggtcgc    1140
ggaggccatg gatgcgatcg ctgcggccga tcttagccag acgagcgggt tcggcccatt    1200
cggaccgcaa ggaatcggtc aatacactac atggcgtgat ttcatatgcg cgattgctga    1260
tccccatgtg tatcactggc aaactgtgat ggacgacacc gtcagtgcgt ccgtcgcgca    1320
ggctctcgat gagctgatgc tttgggccga ggactgcccc gaagtccggc acctcgtgca    1380
cgcggatttc ggctccaaca atgtcctgac ggacaatggc cgcataacag cggtcattga    1440
ctggagcgag gcgatgttcg ggattcccaa atacgaggtc gccaacatct tcttctggag    1500
gccgtggttg gcttgtatgg agcagcagac gcgctacttc gagcggaggc atccggagct    1560
tgcaggatcg ccgcggctcc gggcgtatat gctccgcatt ggtcttgacc aactctatca    1620
gagcttggtt gacggcaatt tcgatgatgc agcttgggcg cagggtcgat gcgacgcaat    1680
cgtccgatcc ggagccggga ctgtcgggcg tacacaaatc gcccgcagaa gcgcggccgt    1740
ctggaccgat ggctgtgtag aagtactcgc cgatagtgga aaccgacgcc ccagcactcg    1800
tccgagggca aaggaataga gtagatgccg accgaacaag agctgatttc gagaacgcct    1860
```

```
cagccagcaa ctcgcgcgag cctagcaagg caaatgcgag agaacggcct tacgcttggt  1920
ggcacagttc tcgtccacag ttcgctaagc tcgctcggct gggtcgcggg agggccggtc  1980
gcagtgattc aggcccttct ggattgtgtt ggtccccagg gcacgattgt catgcccacg  2040
cactcgggtg atctgactga tcccgcagat tggagatcgc cgcccgtgcc tgccgattgg  2100
gtgcagatct agagctcgct gatccggcca ttagccatat tattcattgg ttatatagca  2160
taaatcaata ttggctattg gccattgcat acgttgtatc catatcataa tatgtacatt  2220
tatattggct catgtccaac attaccgcca tgttgacatt gattattgac tagttattaa  2280
tagtaatcaa ttacggggtc attagttcat agcccatata tggagttccg cgttacataa  2340
cttacggtaa atggcccgcc tggctgaccg cccaacgacc cccgcccatt gacgtcaata  2400
atgacgtatg ttcccatagt aacgccaata gggactttcc attgacgtca atgggtggag  2460
tatttacggt aaactgccca cttggcagta catcaagtgt atcatatgcc aagtacgccc  2520
cctattgacg tcaatgacgg taaatggccc gctggcatt atgcccagta catgacctta  2580
tgggactttc ctacttggca gtacatctac gtattagtca tcgctattac catggtgatg  2640
cggttttggc agtacatcaa tgggcgtgga tagcggtttg actcacgggg atttccaagt  2700
ctccacccca ttgacgtcaa tgggagtttg ttttggcacc aaaatcaacg ggactttcca  2760
aaatgtcgta caactccgc cccattgacg caaatgggcg gtaggcgtgt acggtgggag  2820
gtctatataa gcagagctct ctggctaact agagaaccca ctgcttactg gcttatcgaa  2880
attaatacga ctcactatag ggagacccaa gctggctagc accatgcata acacaaagaa  2940
tcaccctatg ctcatgaacc tgctgaagga caatcctgcc caggacaccg gttcaaagct  3000
tggtaccatg gatcctcgcg cctcctccaa ttcactggcc gtcgttttac aagaggcccg  3060
caccgatcgc ccttcccaac agttgcgcag cctgaatggc gaatgcgct ttgcctggtt  3120 tccggcacca gaagcggtgc cggaaagctg gctggagtgc gatcttcctg aggccgatac  3180
tgtcgtcgtc ccctcaaact ggcagatgca cggttacgat gcgcccatct acaccaacgt  3240
gacctatccc attacggtca atccgccgtt tgttcccacg gagaatccga cgggttgtta  3300
ctcgctcaca tttaatgttg atgaaagctg gctacaggaa ggccagacgc gaattatttt  3360
tgatggcgtt aactcggcgt ttcatctgtg gtgcaacggg cgctgggtcg gttacggcca  3420
ggacagtcgt ttgccgtctg aatttgacct gagcgcattt ttacgcgccg gagaaaaccg  3480
cctcgcggtg atggtgctgc gctggagtga cggcagttat ctggaagatc aggatatgtg  3540
gcggatgagc ggcattttcc gtgacgtctc gttgctgcat aaaccgacta cacaaatcag  3600
cgatttccat gttgccactc gctttaatga tgatttcagc cgcgctgtac tggaggctga  3660
agttcagatg tgcggcgagt tgcgtgacta cctacgggta acagtttctt tatggcaggg  3720
tgaaacgcag gtcgccagcg gcaccgcgcc tttcggcggt gaaattatcg atgagcgtgg  3780
tggttatgcc gatcgcgtca cactacgtct gaacgtcgaa acccgaaac tgtggagcgc  3840 cgaaatcccg aatctctatc gtgcggtggt tgaactgcac accgccgacg gcacgctgat  3900
tgaagcagaa gcctgcgatg tcggtttccg cgaggtgcgg attgaaaatg gtctgctgct  3960
gctgaacggc aagccgttgc tgattcgagg cgttaaccgt cacagcatc atcctctgca  4020 tggtcaggtc atggatgagc agacgatggt gcaggatatc ctgctgatga agcagaacaa  4080
ctttaacgcc gtgcgctgtt cgcattatcc gaaccatccg ctgtggtaca cgctgtgcga  4140
ccgctacggc ctgtatgtgg tggatgaagc caatattgaa acccacggca tggtgccaat  4200
gaatcgtctg accgatgatc cgcgctggct accggcgatg agcgaacgcg taacgcgaat  4260
```

```
ggtgcagcgc gatcgtaatc acccgagtgt gatcatctgg tcgctgggga atgaatcagg    4320
ccacggcgct aatcacgacg cgctgtatcg ctggatcaaa tctgtcgatc cttcccgccc    4380
ggtgcagtat gaaggcggcg gagccgacac cacggccacc gatattattt gcccgatgta    4440
cgcgcgcgtg gatgaagacc agcccttccc ggctgtgccg aaatggtcca tcaaaaaatg    4500
gctttcgcta cctggagaga cgcgcccgct gatcctttgc gaatacgccc acgcgatggg    4560
taacagtctt ggcggtttcg ctaaatactg gcaggcgttt cgtcagtatc cccgtttaca    4620
gggcggcttc gtctgggact gggtggatca gtcgctgatt aaatatgatg aaaacggcaa    4680
cccgtggtcg gcttacggcg gtgattttgg cgatacgccg aacgatcgcc agttctgtat    4740
gaacggtctg gtctttgccg accgcacgcc gcatccagcg ctgacggaag caaaacacca    4800
gcagcagttt ttccagttcc gtttatccgg gcaaaccatc gaagtgacca gcgaatacct    4860
gttccgtcat agcgataacg agctcctgca ctggatggtg gcgctggatg gtaagccgct    4920
ggcaagcggt gaagtgcctc tggatgtcgc tccacaaggt aaacagttga ttgaactgcc    4980
tgaactaccg cagccggaga cgccgggca actctggctc acagtacgcg tagtgcaacc    5040
gaacgcgacc gcatggtcag aagccggcca catcagcgcc tggcagcagt ggcgtctggc    5100
ggaaaacctc agtgtgacgc tccccgccgc gtcccacgcc atcccgcatc tgaccaccag    5160
cgaaatggat ttttgcatca agctgggtaa taagcgttgg caatttaacc gccagtcagg    5220
ctttcttcca cagatgtgga ttggcgataa aaaacaactg ctgacgccgc tgcgcgatca    5280
gttcacccgt gcaccgctgg ataacgacat ggcgtaagt gaagcgaccc gcattgaccc    5340
taacgcctgg gtcgaacgct ggaaggcggc gggccattac caggccgaag cagcgttgtt    5400
gcagtgcacg gcagatacac ttgctgacgc ggtgctgatt acgaccgctc acgcgtggca    5460
gcatcagggg aaaaccttat ttatcagccg gaaaacctac cggattgatg gtagtggtca    5520
aatggcgatt accgttgatg ttgaagtggc gagcgataca ccgcatccgg cgcggattgg    5580
cctgaactgc cagctggcgc aggtagcaga gcgggtaaac tggctcggat tagggccgca    5640
agaaaactat cccgaccgcc ttactgccgc ctgttttgac cgctgggatc tgccattgtc    5700
agacatgtat accccgtacg tcttcccgag cgaaaacggt ctgcgctgcg ggacgcgcga    5760
attgaattat ggcccacacc agtggcgcgg cgacttccag ttcaacatca gccgctacag    5820
tcaacagcaa ctgatggaaa ccagccatcg ccatctgctg cacgcggaag aaggcacatg    5880
gctgaatatc gacggtttcc atatggggat tggtggagac gactcctgga gcccgtcagt    5940
atcggcggaa ttacagctga gcgccggtcg ctaccattac cagttggtct ggtgtcaaaa    6000
agcggccgca gatccaaaaa agaagagaaa ggtagatcca aaaagaaga gaaaggtaga    6060 tccaaaaaag aagagaaagg tagatacggc cctcgagcct cccccagtgt ccaagaggga    6120
atccaaatcc aggtcgcgat cgaagagtcc ccccaagtct cctgaagagg aaggagcggt    6180
gtcctcttct aggggtcttt cccctctcgc caaaggaatg caaggtctgt tgaatgtcgt    6240
gaaggaagca gttcctctgg aagcttcttg aagacaaaca acgtctgtag cgaccctttg    6300
caggcagcgg aaccccccac ctggcgacag gtgcctctgc ggccaaaagc cacccttaat    6360
ggcctaacat cgataaaata aaagatttta tttagtctcc agaaaagggg gggaatgaaa    6420
gaccccacct gtaggtttgg caagctagct taagtaacgc cattttgcaa ggcatggaaa    6480
aatacataac tgagaataga gaagttcaga tcaaggtcag gaacagatgg aacagctgaa    6540
tatgggccaa acaggatatc tgtggtaagc agttcctgcc ccggctcagg gccaagaaca    6600
gatggaacag ctgaatatgg gccaaacagg atatctgtgg taagcagttc ctgccccggc    6660
```

```
tcagggccaa gaacagatgg tccccagatg cggtccagcc ctcagcagtt tctagagaac    6720
catcagatgt ttccagggtg ccccaaggac ctgaaatgac cctgtgcctt atttgaacta    6780
accaatcagt tcgcttctcg cttctgttcg cgcgcttctg ctccccgagc tcaataaaag    6840
agcccacaac ccctcactcg gggcgccagt cctccgattg actgagtcgc ccgggtaccc    6900
gtgtatccaa taaaccctct tgcagttgca tccgacttgt ggtctcgctg ttccttggga    6960
gggtctcctc tgagtgattg actaccgtc agcggggtc tttcatttgg ggctcgtcc       7020
gggatcggga gacccctgcc cagggaccac cgacccacca ccgggaggta agctggctgc    7080
ctcgcgcgtt tcggtgatga cggtgaaaac ctctgacaca tgcagctccc ggagacggtc    7140
acagcttgtc tgtaagcgga tgccgggagc agacaagccc gtcagggcgc gtcagcgggt    7200
gttggcgggt gtcggggcgc agccatgacc cagtcacgta gcgatagcgg agtgtatact    7260
ggcttaacta tgcggcatca gagcagattg tactgagagt gcaccatatg cggtgtgaaa    7320
taccgcacag atgcgtaagg agaaaatacc gcatcaggcg ctcttccgct tcctcgctca    7380
ctgactcgct gcgctcggtc gttcggctgc ggcgagcggt atcagctcac tcaaaggcgg    7440
taatacggtt atccacagaa tcaggggata cgcaggaaa gaacatgtga gcaaaaggcc    7500
agcaaaaggc caggaaccgt aaaaaggccg cgttgctggc gttttccat aggctccgcc    7560
cccctgacga gcatcacaaa aatcgacgct caagtcagag gtggcgaaac ccgacaggac    7620
tataaagata ccaggcgttt ccccctggaa gctccctcgt gcgctctcct gttccgaccc    7680
tgccgcttac cggatacctg tccgcctttc tcccttcggg aagcgtggcg ctttctcata    7740
gctcacgctg taggtatctc agttcggtgt aggtcgttcg ctccaagctg ggctgtgtgc    7800
acgaaccccc cgttcagccc gaccgctgcg ccttatccgg taactatcgt cttgagtcca    7860
acccggtaag acacgactta tcgccactgg cagcagccac tggtaacagg attagcagag    7920
cgaggtatgt aggcggtgct acagagttct tgaagtggtg gcctaactac ggctacacta    7980
gaaggacagt atttggtatc tgcgctctgc tgaagccagt taccttcgga aaaagagttg    8040
gtagctcttg atccggcaaa caaaccaccg ctggtagcgg tggttttttt gtttgcaagc    8100
agcagattac gcgcagaaaa aaaggatctc aagaagatcc tttgatcttt tctacggggt    8160
ctgacgctca gtggaacgaa aactcacgtt aagggatttt ggtcatgaga ttatcaaaaa    8220
ggatcttcac ctagatcctt ttaaattaaa aatgaagttt taaatcaatc taagtatat    8280
atgagtaaac ttggtctgac agttaccaat gcttaatcag tgaggcacct atctcagcga    8340
tctgtctatt tcgttcatcc atagttgcct gactccccgt cgtgtagata actacgatac    8400
gggagggctt accatctggc cccagtgctg caatgatacc gcgagaccca cgctcaccgg    8460
ctccagattt atcagcaata aaccagccag ccggaagggc cgagcgcaga gtggtcctg    8520
caactttatc cgcctccatc cagtctatta attgttgccg ggaagctaga gtaagtagtt    8580
cgccagttaa tagtttgcgc aacgttgttg ccattgctgc aggcatcgtg gtgtcacgct    8640
cgtcgtttgg tatggcttca ttcagctccg gttcccaacg atcaaggcga gttacatgat    8700
cccccatgtt gtgcaaaaaa gcggttagct ccttcggtcc tccgatcgtt gtcagaagta    8760
agttggccgc agtgttatca ctcatggtta tggcagcact gcataattct cttactgtca    8820
tgccatccgt aagatgcttt tctgtgactg gtgagtactc aaccaagtca ttctgagaat    8880
agtgtatgcg gcgaccgagt tgctcttgcc cggcgtcaac acgggataat accgcgccac    8940
atagcagaac tttaaaagtg ctcatcattg gaaaacgttc ttcggggcga aaactctcaa    9000
ggatcttacc gctgttgaga tccagttcga tgtaacccac tcgtgcaccc aactgatctt    9060
```

```
cagcatcttt tactttcacc agcgtttctg ggtgagcaaa aacaggaagg caaaatgccg    9120 caaaaaggg aataagggcg acacggaaat gttgaatact catactcttc cttttcaat     9180 attattgaag catttatcag ggttattgtc tcatgagcgg atacatattt gaatgtattt    9240
agaaaaataa acaaatagggg gttccgcgca catttcccg aaaagtgcca cctgacgtct    9300
aagaaaccat tattatcatg acattaacct ataaaaatag gcgtatcacg aggccctttc   9360
gtcttcaaga attcatacca gatcaccgaa aactgtcctc caaatgtgtc cccctcacac   9420
tcccaaattc gcgggcttct gcctcttaga ccactctacc ctattcccca cactcaccgg   9480
agccaaagcc gcggccttc cgtttcttg cttttgaaag accccacccg taggtggcaa    9540
gctagcttaa gtaacgccac tttgcaaggc atggaaaaat acataactga gaatagaaaa   9600
gttcagatca aggtcaggaa caaagaaaca gctgaatacc aaacaggata tctgtggtaa   9660
gcggttcctg ccccggctca gggccaagaa cagatgagac agctgagtga tgggccaaac   9720
aggatatctg tggtaagcag ttcctgcccc ggctcggggc caagaacaga tggtccccag   9780
atgcggtcca gccctcagca gtttctagtg aatcatcaga tgtttccagg gtgccccaag   9840
gacctgaaaa tgaccctgta ccttatttga actaaccaat cagttcgctt ctcgcttctg   9900
ttcgcgcgct tccgctctcc gagctcaata aaagagccca caaccctca ctcggcgcgc   9960 cagtcttccg atagactgcg tcgcccgggt acccgtattc ccaataaagc ctcttgctgt   10020
ttgcatccga atcgtggtct cgctgttcct tgggagggtc tcctctgagt gattgactac   10080
ccacgacggg ggtctttcat ttgggggctc gtccgggatt tggagacccc tgcccaggga   10140
ccaccgaccc accaccggga ggtaagctgg ccagcaactt atctgtgtct gtccgattgt    10200
ctagtgtcta tgtttgatgt tatgcgcctg cgtctgt                              10237
```